(12) United States Patent
Tsai

(10) Patent No.: US 7,083,581 B2
(45) Date of Patent: Aug. 1, 2006

(54) MULTI-FUNCTIONAL MASSAGER

(76) Inventor: Chin-Yi Tsai, P.O. Box 82-144, Taipei (TW)

( * ) Notice: Subject to any disclaimer, the term of this patent is extended or adjusted under 35 U.S.C. 154(b) by 161 days.

(21) Appl. No.: 10/796,101

(22) Filed: Mar. 10, 2004

(65) Prior Publication Data

US 2005/0203445 A1    Sep. 15, 2005

(51) Int. Cl.
*A61H 15/02* (2006.01)
*A61H 23/02* (2006.01)
*A61H 1/00* (2006.01)

(52) U.S. Cl. ................. 601/15; 601/111; 601/125; 601/135

(58) Field of Classification Search ............ 601/15–21, 601/27, 30, 46, 49, 51–53, 64, 69, 70, 80, 601/84, 86, 87, 90, 93–95, 97–99, 101–104, 601/111, 116, 125–129, 130, 135; 607/3, 607/96, 98–100
See application file for complete search history.

(56) References Cited

U.S. PATENT DOCUMENTS

| 5,336,159 | A | * | 8/1994 | Cheng | 601/15 |
| 6,053,881 | A | * | 4/2000 | Boodramsingh et al. | 601/70 |
| 2003/0125647 | A1 | * | 7/2003 | Lin | 601/15 |
| 2005/0043655 | A1 | * | 2/2005 | Schenck | 601/15 |

* cited by examiner

*Primary Examiner*—Quang D. Thanh
(74) *Attorney, Agent, or Firm*—Leong C. Lei

(57) ABSTRACT

A massager having a massaging head and a handle, the handle being arch-shaped having two ends connected to the massaging head with massaging function, characterized in that the massaging face at the bottom section of the massaging head is provided with a vibration beating section, rollers, radiation section and low frequency conducting head, the interior of the massaging head has a motor via a reciprocation device which is connected to an impaction base seat having protrusions so as to form the vibration beating section.

6 Claims, 6 Drawing Sheets

US 7,083,581 B2

MULTI-FUNCTIONAL MASSAGER

BACKGROUND OF THE INVENTION (a) Technical Field of the Invention

The present invention relates to a massager.

(b) Description of the Prior Art

Massaging is a process by applying a force to muscle or the external surface of the human body to release stress or tiredness so as to obtain relaxation. Conventional massaging methods include pressing, traction, kneading, beating, etc so as to relax ligament and muscle so as to enhance blood circulation and speed up metabolism.

Conventional devices for massaging only focus on the surface of the massaging surface of the device without much improvement on the control of massaging. In other words, the massager does not take care of the contacting interface between the human body. Although the conventional massagers could relax the muscle but they causes different problems for instance, the positioning of massaging and the angle of application of the device. Accordingly, it is an object of the present invention to provide multi-functional which mitigates the above drawbacks.

SUMMARY OF THE INVENTION

Accordingly, it is an object of the present invention to provide a massager having a massaging head and a camshaft, the camshaft being arch-shaped having two ends connected to the massaging head with massaging function, characterized in that the massaging face at the bottom section of the massaging head is provided with a vibration beating section, rollers, radiation section and low frequency conducting head, the interior of the massaging head has a motor via a reciprocation device is connected to art impaction base seat having protrusions so as to form the vibration beating section, when the motor is in operation, the reciprocation device causes the impaction base seat to vibrate up and down, and the rollers are mounted between the massager head bottom section and the camshaft and the surface of each roller is provided with protrusions or treads which can stimulate skin, the upward bent lower section of the camshaft is the radiation section mounted with electro-thermal wire or tungsten wire which can produce heat or preheat to the massaging region and the appropriate position of the massaging face is provided with the low frequency conducting heads with protrusions made from conductive rubber or other conductive material and the low frequency conducting head provides multi-stage low frequency current by the low frequency circuit board within the massaging head.

Still yet another object of the present invention is to provide a massager, wherein the middle section of the camshaft is a buffer seat made from a compressible material, the buffer seat has spring pivotal axle connecting two camshaft.

A further object of the present invention is to provide a massager, wherein the buffer seat is provided with a panel for controlling ON/OFF and massaging selection, and a display for displaying control and selection.

Another object of the present invention is to provide a massager, wherein the end of the massaging head has a grip rim suitable for hand grip or finger grip.

Still a further object of the present invention is to provide a massager, wherein a separate base seat is provided to the massager which is engageable and separable with the massaging head and the camshaft, and the base seat allows the massager to be reversely placed flat to provide support for massaging, an insertion plate extended from the camshaft and the massage head allow the base seat to connect with the camshaft, and the corresponding position of the base seat is an insertion slot.

A further object of the present invention is to provide a massager, wherein the material of the roller is a material which mixes with a hyper thermal material which emits far IR radiation.

Still another object of the present invention is to provide a massager, wherein the low frequency IC board is provided with external wire and socket for externally connected to low frequency plaster connected to the body for low frequency massaging.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIGS. 3 & 3A are sectional views of the present invention.

DETAILED DESCRIPTION OF THE PREFERRED EMBODIMENTS

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
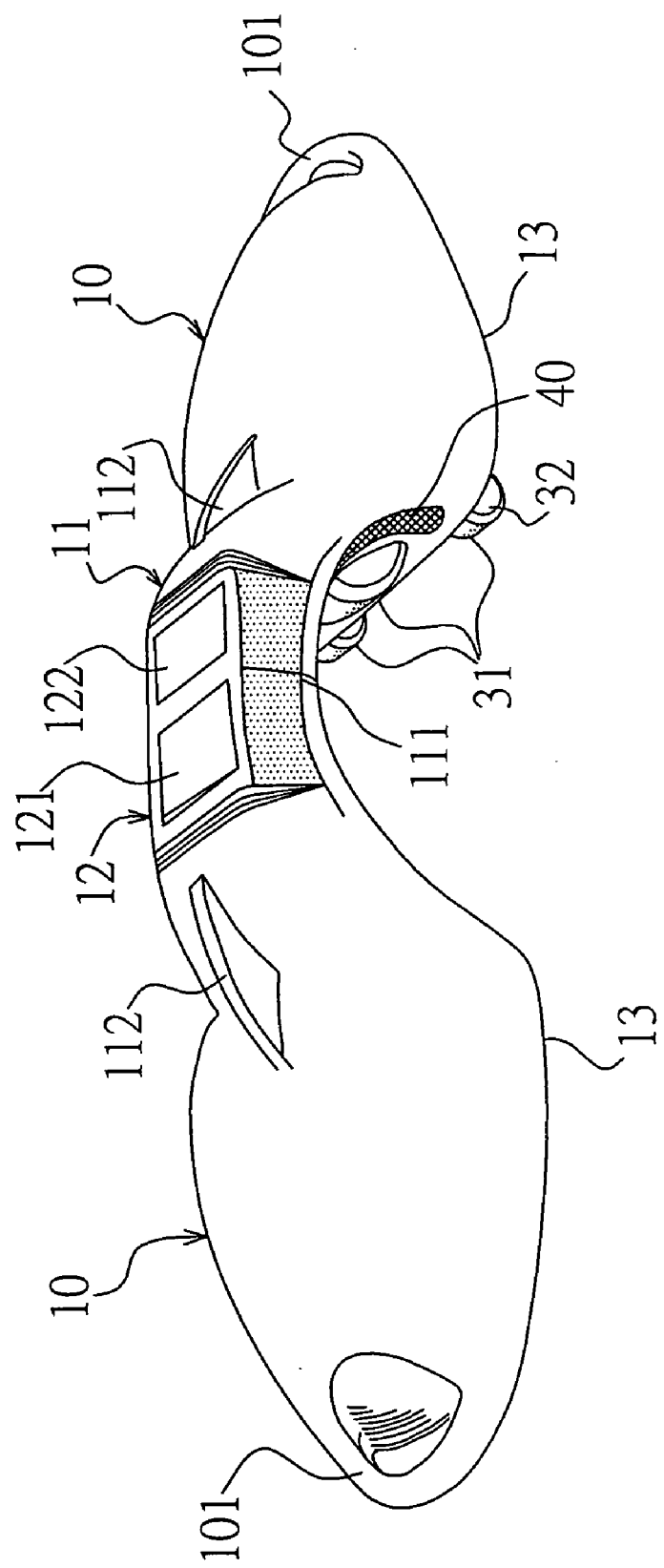
FIG. 1 is a perspective view (top view) of the present invention.
Figure 2:
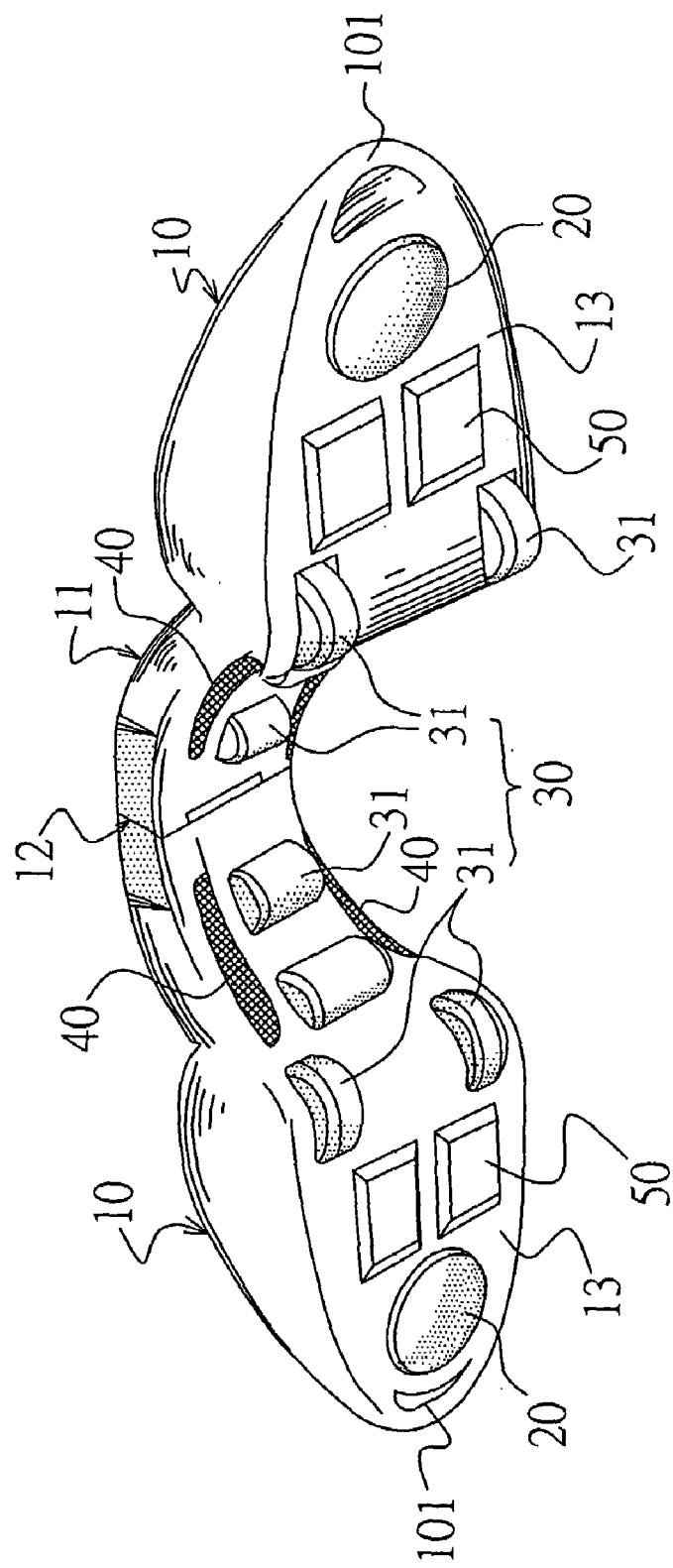
FIG. 2 is a perspective view (bottom view) of the present invention.

Referring to FIGS. 1 and 2, there is shown a massager having its both ends connected to massaging head 10 with massaging function and having a middle connection portion as an arch-shaped handle 11. The handle 11 provides a grip function which also provides a control panel and display panel. The massaging head is functioned as weight balance and extends the massaging function and provides massaging, heating effect.

In appearance the massaging face 13 at the bottom section of the massaging head 10 is provided with a vibration beating section 20, rollers 30, low frequency conduction head 50 such that the skin contacting with the massaging face 13 will subject to vibration beating, pressing and rolling stimulation, and low current electrical stimulation. These stimulations release muscle stress, massaging of skin, blood circulation and releases tiredness, promotes blood circulation and enhances metabolism. The roller 30 is made from a material mixed with a hyper thermal material which emits far infra-red radiation.

Figure 3:
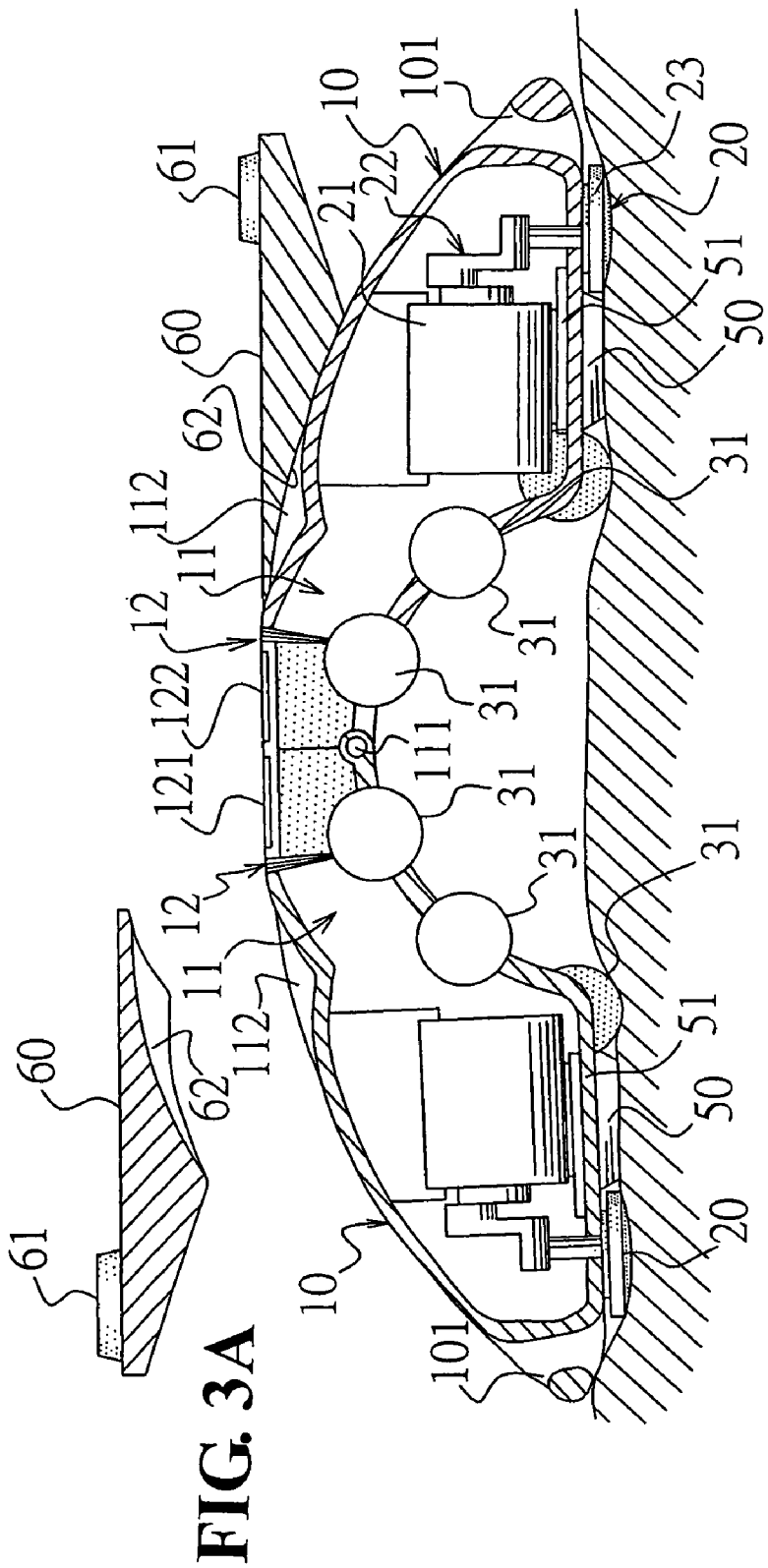

As shown in FIG. 3 and FIG. 3A, the middle section of the handle 11 is provided with a buffer seat 12 made from a compressible material. The upper end of the handle 11 is provided with a control panel 121 and a display panel 122 for controlling ON/OFF, selectors (massagings) (speed of vibration, temperature, low frequency, time duration etc). The display panel displays the control status and the selection status. The buffer seat 12 has spring pivotal shaft connected to two handles 11 such that a plurality of angle can be rotated. The action of the pivotal shaft 111 allows the pivotal shaft to maintain at a specific angle (to maintain two massaging faces on a flat surface). The elastic effect of the pivotal shaft 111 and the buffer seat 12 can be connected such that there is elastic, shock absorbing and compressible between two massaging heads 10.

The end of the massaging head 10 is a grip section which suitable for the gripping of fingers and hand. As shown in the figure, a grip rim 101 is provided. The base seat 60 can be connected wit the massaging head 10 and the handle 11 and has support 61 so that the massager can be reversely placed on a flat surface to provide different massaging function. The engagement of the base seat 60 with the massaging head 10 and the handle 11 depends on the extended insertion plate 112 extended from the top section of the handle 11 and the massaging head 10, and the relative position of the base seat is provided with an insertion slot 62. When the insertion slot 62 and the insertion plate 112 are connected, the base seat 60 can be positioned on a flat surface and can support the entire massager.

Referring to FIG. 3, the entire massager has a massaging head 10 included a motor 21. The motor 21 via the use of a reciprocation device 22 is connected to an impaction base seat 23 protruded from the massaging surface 13, and is formed into a vibration beating section 20. When a motor 21 is in operation, the reciprocation device 22 causes the impaction base seat 23 to generate vibration beating. A plurality of driven rollers 31 are formed between the bottom section of the massaging head 10 and the handle 11. The surface of each roller 31 is provided with protrusions or threads 32, forming into rollers 30. The bottom section of the handle 11 has a thermal radiation section 40 made from electro-thermal wire or tungsten which can produce heat or provide pre-heating. The appropriate position of the massaging face 13 is provided with low frequency conduction head 10 made from conductive rubber or other conductive material. The low frequency IC board 51 within the massaging head 10 provides multi-stages low frequency current.

The material of rollers 31 can mix with a material when encounters with heat, a far IR radiation is emitted such that the roller 31 provides a far IR radiation function.

The low frequency IC board 51 is provided with externally connected wire and insertion holes which can connect to plaster for massaging at other parts of the body.

Figure 4:
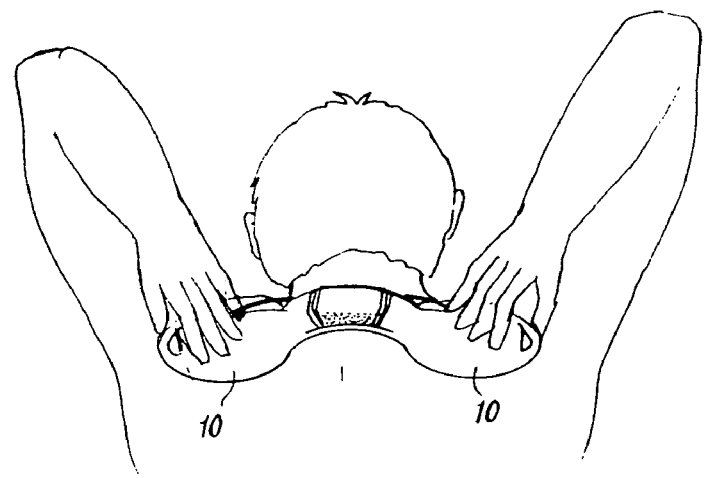
FIGS. 4, 5, 6, 7, 8 and 9 are views showing implementation of the massager of the present invention.

FIG. 4 shows application to massage the shoulder. The user holds the grip section and the massaging face 13 is closely contact with the shoulder to proceed with the massaging.

Figure 5:
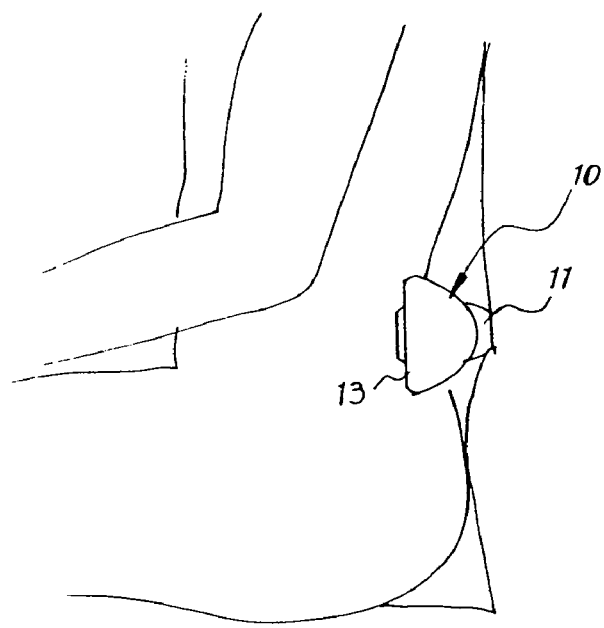

FIG. 5 shows application on waist. The user leans against the massager with the waist contacting with the massaging face 13 to proceed with the massaging.

Figure 6:
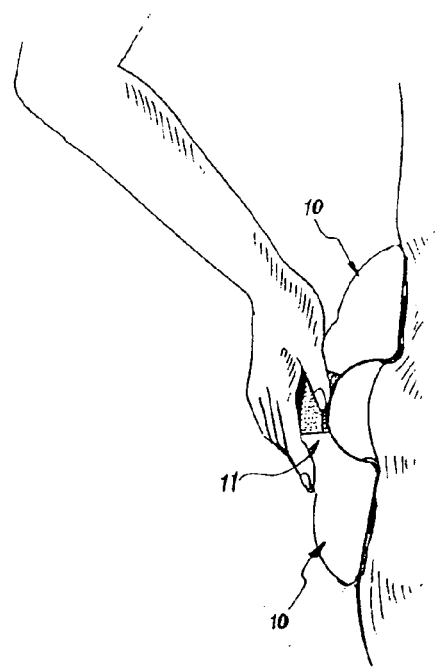

FIG. 6 shows application of massaging to the side of the waist. The user holds the handle 11 and the massaging face 13 contacts with the side of the waist to proceed with the massaging.

Figure 7:
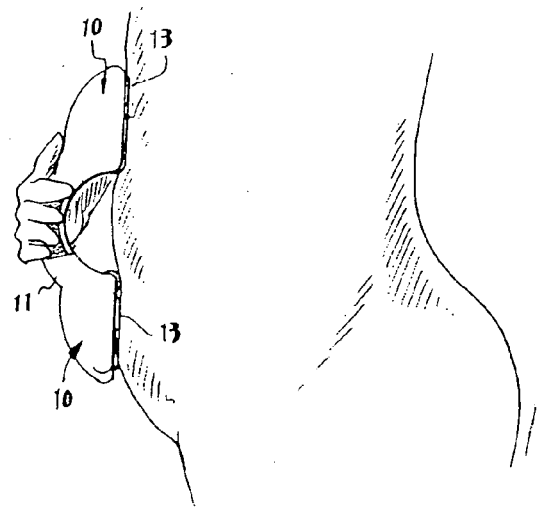

FIG. 7 shows application of the massager to the lower abdomen. The user holds the handle 11 so that the massaging face 13 contacts with the lower abdomen to proceed with massaging.

Figure 8:
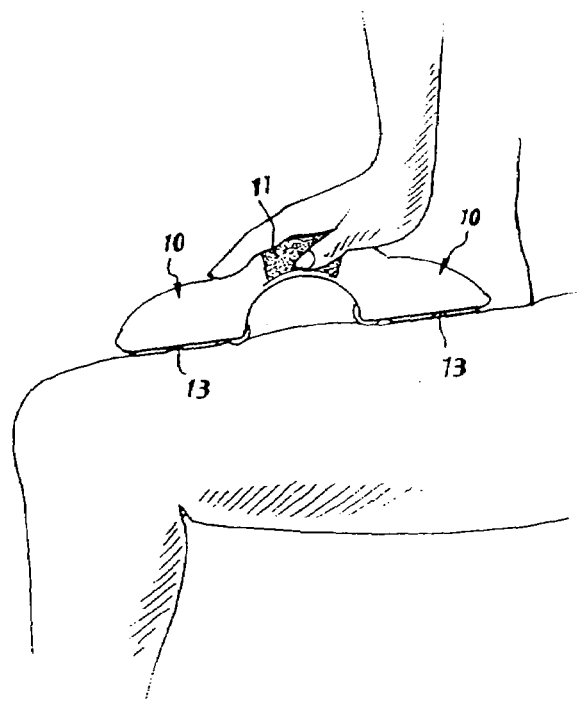

FIG. 8 shows application of the massager to the thigh. The user holds the handle 11 and the massaging face 13 contacts with the thigh to proceed with massaging.

Figure 9:
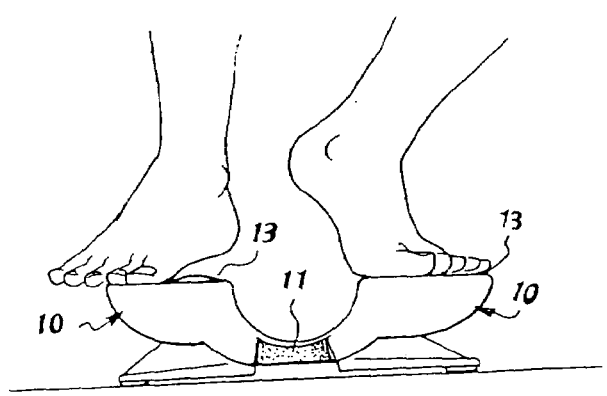

FIG. 9 shows application of the massager to the sole. The massager is reversed at the base seat 60 to place on the ground. The user places the sole on the massaging face 13 to proceed with the massaging.

The position of the radiation 40 provides heating effect and lighting.

If the above functions are operated simultaneously, the muscle of the body is vibrated and beat so that the muscle is stimulated and the protrusion roller 30 will stimulate the blood point. Therefore, the massaging skin is stress released and relax.

The handle 11 having two massaging heads 10 can be held with a single hand to apply onto various part of the body. This will eliminate the weight burden at a certain position.

The inner surface of the handle 11 has a plurality of rollers 31 which can be used to massage shoulder, arm, leg, ankle, etc.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A multi-functional massager comprising:
   massaging heads and a handle, the handle being arch-shaped having two ends each connected to one of the massaging heads;
   wherein each massaging head has a massaging face located at a bottom section of the massaging head, the massaging face is provided with a vibration beating section, a first set of rollers, and low frequency current conducting heads, the massaging head further includes a motor located in the interior of the massage head, a reciprocation device driven by the motor and connected to an impaction base seat protruded from the massaging face so as to form the vibration beating section, whereby when the motor is in operation, the reciprocation device causes the impaction base seat to vibrate up and down;
   a second set of rollers mounted on a bottom section of the handle and the surface of each roller is provided with protrusions or threads which can stimulate the skin of a user;
   a thermal radiation section comprised of electro-thermal wire or tungsten wire, and mounted on an upward bent portion of the bottom section of the handle to produce heat to a massaging region; and
   wherein the low frequency conducting heads of the massaging face each includes protrusion made from conductive rubber or other conductive material and connected to a low frequency circuit board located within the massage head to provide multi-stage low frequency current stimulation.

2. The massager as claimed in claim 1, wherein a middle section of the handle is a buffer seat made from a compressible material, the buffer seat has a spring pivotal axle connecting two portions of the handle.

3. The massager as claimed in claim 2, wherein the buffer seat is provided with a panel for controlling power ON/OFF and massaging selection, and a display for displaying control status and selection status.

4. The massager as claimed in claim 1, wherein one end of massaging head has a grip rim suitable for the gripping of head or fingers.

5. The massager as claimed in claim 1, wherein a separate support base seat is provided to the massager, which is engage able and separable with the massaging head and the handle, the support base seat includes an insertion slot that is connected to an insertion plate extended from the handle and the massage head so that the support base seat allows the massager to be reversely positioned on a flat surface to provide support for massaging action.

6. The massager as claimed in claim 1, wherein each roller is made from a material mixed with a hyper thermal material which emits far infra-red radiation.

* * * * *